United States Patent [19]
Cassidy et al.

[11] Patent Number: 4,782,083
[45] Date of Patent: Nov. 1, 1988

[54] 3,4-DIHYDRO-2H-1-BENZOPYRANS USEFUL AS ANTI-HYPERTENSIVE AGENTS

[75] Inventors: Frederick Cassidy; Geoffrey Stemp; John M. Evans, all of Harlow, England

[73] Assignee: Beecham Group P.L.C., England

[21] Appl. No.: 902,428

[22] Filed: Aug. 29, 1986

[30] Foreign Application Priority Data

Sep. 3, 1985 [GB] United Kingdom ............... 8521857

[51] Int. Cl.$^4$ ............... A61K 31/35; A61K 31/40; A61K 31/445; C07D 311/68; C07D 405/04; C07D 311/70
[52] U.S. Cl. ............................. 514/456; 549/404; 549/399; 549/345; 549/60; 549/57; 549/51; 548/525; 548/454; 548/336; 548/305; 548/236; 548/226; 548/200; 548/195; 548/191; 548/188; 548/184; 548/183; 548/141; 548/136; 548/135; 548/134; 548/130; 548/129; 548/128; 548/127; 546/269; 546/169; 546/159; 546/156; 546/146; 546/143; 546/141; 544/407; 544/406; 544/405; 544/335; 544/334; 544/333; 544/322; 544/298; 544/283; 544/238; 544/219; 544/217; 544/212; 544/180; 514/444; 514/443; 514/422; 514/414; 514/407; 514/406; 514/397; 514/377; 514/376; 514/374; 514/370; 514/369; 514/365; 514/361; 514/337; 514/314; 514/313; 514/312; 514/310; 514/309; 514/307; 514/259; 514/256; 514/255; 514/242
[58] Field of Search ............... 544/405, 406, 407, 335, 544/334, 333, 322, 298, 238, 283, 219, 217, 212, 180; 514/444, 443, 422, 414, 407, 406, 397, 377, 376, 374, 370, 369, 365, 361, 337, 256, 255, 313, 312, 314, 310, 309, 307, 259, 242, 456; 549/404, 399, 345, 51, 57, 60; 546/196, 269, 169, 159, 156, 146, 143, 141; 548/454, 305, 336, 200, 195, 191, 188, 184, 183, 525, 226, 236, 141, 136, 135, 134, 130, 129, 128, 127

[56] References Cited

U.S. PATENT DOCUMENTS 4,481,214  11/1984  Evans .................... 549/404
4,575,511  3/1986   Evans et al. ............ 549/404
4,677,116  6/1987   Evans .................... 549/404

FOREIGN PATENT DOCUMENTS 91748   10/1983  European Pat. Off. .
95316   11/1983  European Pat. Off. .
107423  5/1984   European Pat. Off. .
126311  11/1984  European Pat. Off. .
126350  11/1984  European Pat. Off. .
126367  11/1984  European Pat. Off. .
138134  4/1985   European Pat. Off. .
139992  5/1985   European Pat. Off. .

OTHER PUBLICATIONS

J. March, Advanced Organic Chemistry: Reactions, Mechanisms, and Structure, p. 21 (1968).

Primary Examiner—Nicky Chan
Attorney, Agent, or Firm—Jacobs & Jacobs

[57] ABSTRACT

Compounds of formula (I) and pharmaceutically acceptable salts thereof:

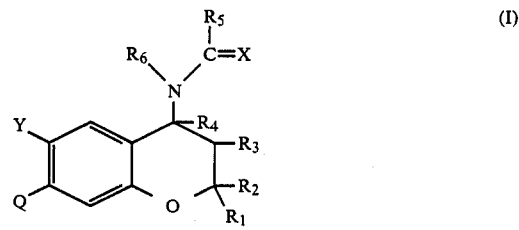

wherein:
one of $R_1$ and $R_2$ is hydrogen or $C_{1-4}$ alkyl and the other is $C_{1-4}$ alkyl or $R_1$ and $R_2$ together are $C_{2-5}$-polymethylene;
either $R_3$ is hydrogen, hydroxy, $C_{1-6}$ alkoxy or $C_{1-7}$ acyloxy and $R_4$ is hydrogen or $R_3$ and $R_4$ together are a bond;
$R_5$ is hydrogen $C_{1-6}$ alkyl optionally substituted by halogen hydroxy, $C_{1-6}$ alkoxy, $C_{1-6}$ alkoxycarbonyl, carboxy or amino optionally substituted by one or two independent $C_{1-6}$ alkyl groups, or $C_{2-6}$ alkenyl, amino optionally substituted by a $C_{1-6}$ alkyl or $C_{1-6}$ alkenyl group or by a $C_{1-6}$ alkanoyl group optionally substituted by up to three halo atoms, by a phenyl group optionally substituted by $C_{1-6}$ alkyl, $C_{1-6}$ alkoxy or halogen, or aryl or heteroaryl, either being optionally substituted by one or more groups or atoms selected from the class of $C_{1-6}$ alkyl, $C_{1-6}$ alkoxy, hydroxy, halogen, trifluoromethyl, nitro, cyano, $C_{1-12}$ carboxylic acyl, or amino or aminocarbonyl optionally substituted by one or two $C_{1-6}$ alkyl groups and $R_6$ is hydrogen on $C_{1-6}$ alkyl, or $R_5$ and $R_6$ together are —$CH_2$—$(CH_2)_n$—$Z$—$(CH_2)_m$— wherein m and n are 0 to 2 such that m+n is 1 or 2 and Z is $CH_2$, O, S or NR wherein R is hydrogen, $C_{1-9}$ alkyl, $C_{2-7}$ alkanoyl, phenyl $C_{1-4}$-alkyl, naphthylcarbonyl, phenylcarbonyl or benzylcarbonyl optionally substituted in the phenyl or naphthyl ring by one or two of $C_{1-6}$ alkyl, $C_{1-6}$ alkoxy or halogen; mono- or bi-cyclic- heteroarylcarbonyl;

X is oxygen or sulphur;

Y and Q are electron withdrawing groups; and the nitrogen-containing group in the 4-position being trans to the $R_3$ group when $R_3$ is hydroxy, $C_{1-6}$ alkoxy or $C_{1-7}$ acyloxy; having blood pressure lowering activity, a process and intermediates for their preparation and their use as pharmaceuticals.

7 Claims, No Drawings

3,4-DIHYDRO-2H-1-BENZOPYRANS USEFUL AS ANTI-HYPERTENSIVE AGENTS

The present invention relates to novel benzopyrans having pharmacological activity, to a process and intermediates for preparing them, to pharmaceutical compositions containing them, and to their use in the treatment of mammals.

European Patent Publications Nos. 76075, 91748, 93535, 95316, 107423, 120427, 126311, 126350, 126367 and 138134 disclose classes of compounds that are described as having blood pressure lowering activity or anti-hypertensive activity.

A class of compounds has now been discovered which are 4-substituted benzopyrans substituted in the 6- and 7-positions by electron withdrawing groups. In addition, such benzopyrans have been found to have blood pressure lowering activity.

Accordingly, the present invention provides a compound of formula (I) or, when the compound of formula (I) contains a salifiable group, a pharmaceutically acceptable salt thereof:

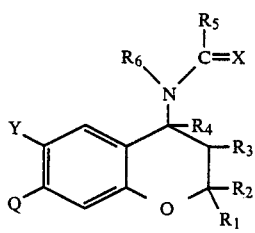

(I)

wherein:

one of $R_1$ and $R_2$ is hydrogen or $C_{1-4}$ alkyl and the other is $C_{1-4}$ alkyl or $R_1$ and $R_2$ together are $C_{2-5}$-polymethylene;

either $R_3$ is hydrogen, hydroxy, $C_{1-6}$ alkoxy or $C_{1-7}$ acyloxy and $R_4$ is hydrogen or $R_3$ and $R_4$ together are a bond;

$R_5$ is hydrogen, $C_{1-6}$ alkyl optionally substituted by halogen, hydroxy, $C_{1-6}$ alkoxy, $C_{1-6}$ alkoxycarbonyl, carboxy or amino optionally substituted by one or two independent $C_{1-6}$ alkyl groups, or $C_{2-6}$ alkenyl, amino optionally substituted by a $C_{1-6}$ alkyl or $C_{1-6}$ alkenyl group or by a $C_{1-6}$ alkanoyl group optionally substituted by up to three halo atoms, by a phenyl group optionally substituted by $C_{1-6}$ alkyl, $C_{1-6}$ alkoxy or halogen, or aryl or heteroaryl, either being optionally substituted by one or more groups or atoms selected from the class of $C_{1-6}$ alkyl, $C_{1-6}$ alkoxy, hydroxy, halogen, trifluoromethyl, nitro, cyano, $C_{1-12}$ carboxylic acyl, or amino or aminocarbonyl optionally substituted by one or two $C_{1-6}$ alkyl groups and $R_6$ is hydrogen or $C_{1-6}$ alkyl, or $R_5$ and $R_6$ together are $-CH_2-(CH_2)_n-Z-(CH_2)_m-$ wherein m and n are 0 to 2 such that m+n is 1 or 2 and Z is $CH_2$, O, S or NR wherein R is hydrogen, $C_{1-9}$ alkyl, $C_{2-7}$ alkanoyl, phenyl $C_{1-4}$-alkyl, naphthylcarbonyl, phenylcarbonyl or benzylcarbonyl optionally substituted in the phenyl or naphthyl ring by one or two of $C_{1-6}$ alkyl, $C_{1-6}$ alkoxy or halogen; mono- or bi-cyclic- heteroarylcarbonyl;

X is oxygen or sulphur;

Y and Q are electron withdrawing groups; and the nitrogen-containing group in the 4-position being trans to the $R_3$ group when $R_3$ is hydroxy, $C_{1-6}$ alkoxy or $C_{1-7}$ acyloxy.

Preferably, $R_1$ and $R_2$ are both $C_{1-4}$ alkyl, in particular both methyl.

When $R_3$ is $C_{1-6}$ alkoxy and $R_4$ is hydrogen, preferred examples of $R_3$ include methoxy and ethoxy, of which methoxy is more preferred. When $R_3$ is $C_{1-7}$ acyloxy and $R_4$ is hydrogen, a preferred class of $R_3$ is unsubstituted carboxylic acyloxy, such as unsubstituted aliphatic acyloxy. However, it is more preferred that $R_3$ and $R_4$ together are a bond, or that $R_3$ and $R_4$ are both hydrogen, or, in particular, that $R_3$ is hydroxy and $R_4$ is hydrogen.

Examples of $R_5$, when $C_{1-6}$ alkyl, include methyl, ethyl and n- and iso-propyl. Preferably such $R_5$ is methyl.

A sub-group of $R_5$, when $C_{1-6}$ alkyl substituted by halogen is $C_{1-6}$ alkyl substituted by chloro or bromo. Examples thereof include methyl or ethyl terminally substituted by chloro or bromo.

Examples of $R_5$, when $C_{1-6}$ alkyl substituted by hydroxy, include methyl or ethyl terminally substituted by hydroxy.

A sub-group of $R_5$, when $C_{1-6}$ alkyl substituted by alkoxy is $C_{1-6}$ alkyl substituted by methoxy or ethoxy. Examples thereof include methyl or ethyl terminally substituted by methoxy or ethoxy.

A sub-group of $R_5$, when $C_{1-6}$ alkyl substituted by $C_{1-6}$ alkoxycarbonyl is $C_{1-6}$ alkyl substituted by methoxycarbonyl or ethoxycarbonyl. Examples thereof include methyl or ethyl terminally substituted by methoxycarbonyl or ethoxycarbonyl.

Examples of $R_5$, when $C_{1-6}$ alkyl substituted by carboxy include methyl or ethyl terminally substituted by carboxy.

Examples of $R_5$ when alkyl substituted by amino optionally substituted by one or two independent $C_{1-6}$ alkyl groups include a group $(CH_2)_nNR_7R_8$ where n is 1 to 6, and $R_7$ and $R_8$ are each independently hydrogen or $C_{1-6}$ alkyl. Examples of n include 1 and 2, in particular 1. Preferably $R_7$ and $R_8$ are each independently selected from hydrogen and methyl. Examples of $R_5$, when $C_{2-6}$ alkenyl include vinyl, prop-1-enyl, prop-2-enyl, 1-methylvinyl, but-1-enyl, but-2-enyl, but-3-enyl, 1-methylenepropyl, or 1-methylprop-2-enyl, in both their E and Z forms where stereoisomerism exists.

Examples of $R_5$ when amino optionally substituted as hereinbefore defined include an amino optionally substituted by a methyl, ethyl, propyl, butyl, allyl or trichloroacetyl group or by a phenyl group optionally substituted by one methyl, methoxy or chloro group or atom, in particular amino, methylamino, and phenylamino optionally substituted in the phenyl ring by one methyl, methoxy or chloro group or atom.

Examples of $R_5$ when aryl include phenyl and naphthyl, of which phenyl is preferred.

A sub-group of $R_5$ heteroaryl is 5- or 6-membered monocyclic or 9- or 10-membered bicyclic heteroaryl of which 5- or 6-membered monocyclic heteroaryl is preferred. In addition, 5- or 6-membered monocyclic or 9- or 10-membered bicyclic heteroaryl preferably contains one, two or three heteroatoms which are selected from the class of oxygen, nitrogen and sulphur and which, in the case of there being more than one heteroatom, are the same or different.

Examples of 5- or 6-membered monocyclic heteroaryl containing one, two or three heteroatoms which are selected from the class of oxygen, nitrogen and sulphur include furyl, thienyl, pyrryl, oxazolyl, thiazolyl, imidazolyl and thiadiazolyl, and pyridyl, pyridazyl, pyrimidyl, pyrazyl and triazyl. Preferred examples of such groups include furanyl, thienyl, pyrryl and pyridyl, in particular 2- and 3-furyl, 2- and 3-pyrryl, 2- and 3-thienyl, and 2-, 3- and 4-pyridyl.

Examples of 9- or 10-membered bicyclic heteroaryl containing one, two or three heteroatoms which are selected from the class of oxygen, nitrogen and sulphur include benzofuranyl, benzothienyl, indolyl and indazolyl, quinolyl and isoquinolyl, and quinazonyl. Preferred examples of such groups include 2- and 3-benzofuryl, 2- and 3-benzothienyl, and 2- and 3-indolyl, and 2- and 3-quinolyl.

Preferably, the number of groups or atoms for optional substitution of aryl or heteroaryl is one, two, three or four.

Preferred examples of the groups or atoms for optional substitution of aryl or heteroaryl include methyl, methoxy, hydroxy, chloro, nitro or cyano.

A sub-group of $R_5$ is phenyl or naphthyl or a 5- or 6-membered monocyclic or a 9- or 10-membered bicyclic heteroaryl, the phenyl, naphthyl or heteroaryl group being optionally substituted by one, two, three or four groups or atoms selected from the class of $C_{1-6}$ alkyl, $C_{1-6}$ alkoxy, halogen, trifluoromethyl, nitro or cyano.

A preferred subgroup of phenyl optionally substituted as hereinbefore defined is phenyl, 4-substituted phenyl, 3-substituted phenyl, 3,4-disubstituted phenyl and 3,4,5-trisubstituted phenyl.

A preferred sub-group of 5- or 6-membered monocyclic or 9- or 10-membered bicyclic heteroaryl optionally substituted as hereinbefore defined is unsubstituted or mono-substituted 5- or 6-membered monocyclic or 9- or 10-membered bicyclic heteroaryl, in particular unsubstituted 5- or 6-membered monocyclic or 9- or 10-membered bicyclic heteroaryl.

$R_5$ and $R_6$, when together are $-CH_2-(CH_2)_n-Z-(CH_2)_m-$ as defined the resulting radical substituting the benzopyran in the 4-position is preferably either pyrrolidinyl or piperidinyl.

When Z is other than $CH_2$, m is often 0 or 1 and n is often 0 or 1. Suitable examples of R when Z is NR include hydrogen, methyl, ethyl, n- and iso-propyl, n-, sec- and tert- butyl, benzyl, phenylcarbonyl or benzylcarbonyl optionally substituted in the phenyl ring by methyl, methoxy, chloro or bromo; furylcarbonyl, thienylcarbonyl, pyrrolylcarbonyl or indolylcarbonyl. Preferably R is hydrogen, methyl, n-butyl, acetyl, benzyl, benzylcarbonyl, phenylcarbonyl or furylcarbonyl. More preferably R is methyl.

Preferred examples of $R_5$ and $R_6$ are $R_5$ methyl and $R_6$ hydrogen and $R_5$ and $R_6$ together are $C_3$ or $C_4$ polymethylene.

Preferably, X is oxygen.

Suitable values for Y and Q include halo, such as chloro and bromo; cyano; nitro; CHO; $C_{2-7}$ alkanoyl, such as $COCH_3$ and $C_{1-6}$ alkoxycarbonyl, such as $CO_2CH_3$.

Preferably Y and Q are different groups, selected from bromo, cyano and nitro.

Examples of a pharmaceutically acceptable salt of a compound of formula (I), when the compound contains a salifiable group which is an optionally substituted amino group, include acid addition salts such as the hydrochloride and hydrobromide salts. Such a salifiable group may be within an $R_5$ group. A carboxy group within $R_5$ may also be salified to form metal salts, such as alkali metal salts, or optionally substituted ammonium salts.

The compounds of formula (I) may also exist as hydrates and the invention extends to these.

The compounds of formula (I), wherein $R_3$ is hydrogen, hydroxy, $C_{1-6}$ alkoxy or $C_{1-7}$ acyloxy and $R_4$ is hydrogen, are asymmetric, and, therefore, can exist in the form of optical isomers. The present invention extends to all such isomers individually and as mixtures, such as racemates.

Examples of compounds of formula (I) include the compounds prepared in the Examples hereinafter.

The present invention also provides a process for the preparation of a compound of formula (I) or, when the compound of formula (I) contains a salifiable group, a pharmaceutically acceptable salt thereof, which comprises acylating a compound of formula (II):

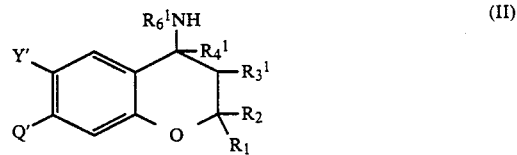

wherein Y' and Q' are Y and Q or groups convertible thereto, $R_1$ and $R_2$ are as hereinbefore defined, $R_3^1$ is hydroxy, $C_{1-6}$ alkoxy or $C_{1-7}$ acyloxy, and $R_6^1$ is hydrogen or $C_{1-6}$ alkyl, the $R_6^1NH$ group being trans to the $R_3^1$ group, with (a) an acylating agent of formula (III):

$$R_9\text{-CO-}L_1 \qquad (III)$$

wherein $L_1$ is a leaving group, and $R_9$ is hydrogen, $C_{1-6}$ alkyl optionally substituted by halogen, hydroxy, $C_{1-6}$ alkoxy, $C_{1-6}$ alkoxycarbonyl, carboxy or amino optionally substituted as hereinbefore defined for $R_5$, $C_{2-6}$ alkenyl or optionally substituted aryl or heteroaryl as hereinbefore defined for $R_5$, or a group convertible to $R_5$ as hereinbefore defined; or (b) a compound of formula (IV)

$$X=C=N.R_{10} \qquad (IV)$$

wherein $R_{10}$ is hydrogen, $C_{1-6}$ alkyl, $C_{1-6}$ alkenyl, $C_{1-6}$ alkanoyl optionally substituted by up to three halo atoms, or phenyl optionally substituted by $C_{1-6}$ alkyl, $C_{1-6}$ alkoxy or halogen; and X is oxygen or sulphur, and thereafter when $R_{10}$ is hydrogen, optionally converting $R_{10}$;

and thereafter, optionally and as necessary, and in any appropriate order, performing the following steps: when $R_6$ is hydrogen and $R_9$ is $G(CH_2)_zL$, where z is 3 or 4, and G is a leaving group, cyclising the resultant compound; optionally converting Y' and /or Q' to a Y and/or Q group; optionally converting $R_3$ in the resulting compound into another $R_3$; in the case where $R_3$ and $R_4$ in the resulting compound are hydroxy and hydrogen respectively, optionally dehydrating the compound to give another compound wherein $R_3$ and $R_4$ together are a bond, and optionally reducing the resulting compound wherein $R_3$ and $R_4$ together are a bond, to give another compound, wherein $R_3$ and $R_4$ are each hydrogen; and optionally thiating the $R_6-N-CO-R_5$ group in the resulting compound to give a compound wherein X is sulphur; and when the resulting compound of formula (I) contains a salifiable group, optionally forming a pharmaceutically acceptable salt thereof.

In the process variant (a) acylation of a compound of formula (II) with an acylating agent of formula (III), the leaving group $L_1$ is a group that is displaceable by a primary or secondary amino nucleophile. Examples of such a group include $C_{1-4}$ alkanoyloxy, and halogen, such as chloro and bromo. When the leaving group $L_1$ is either of these examples, the acylating agent of formula (III) is either an acid anhydride or an acid halide. When it is an acid anhydride, it may be a mixed or simple anhydride. If it is a mixed anhydride, it may be prepared in situ from a carboxylic acid and an acid halide, although this is less preferred than using the halide itself.

In process variant (a), when $R_5$ in the desired compound of formula (I) is an $R_5$ optionally substituted amino-substituted alkyl group as hereinbefore defined, it is preferred that $R_9$ is a group convertible to the $R_5$ substituted alkyl group as hereinbefore defined, in particular that it is $C_{1-6}$ alkyl substituted by halo, especially bromo. The $R_9$ halo substituent in the resultant compound of process variant (a) may be converted to an $R_5$ substituent which is amino optionally substituted as hereinbefore defined by a conventional amination reaction with ammonia or a corresponding alkyl- or dialkylamine.

Less favourably $R_9$ may be $C_{1-6}$ alkyl substituted by protected amino, protected $C_{1-6}$ alkylamino or amino substituted by two independent $C_{1-6}$ alkyl groups, it being necessary to protect the $R_9$ amino function in process variant (a).

When the acylating agent of formula (III) is an acid anhydride, the acylation of the compound of formula (II) may be carried out in the presence of an acid acceptor, such as sodium acetate, optionally using the anhydride as the solvent.

When the acylating agent of formula (III) is an acid halide, the acylation of the compound of formula (II) is, preferably, carried out in a non-aqueous medium, such as dichloromethane, in the presence of an acid acceptor, such as triethylamine, trimethylamine, pyridine, picoline or calcium, potassium or sodium carbonate.

When $R_3^1$ in a compound of formula (II) is hydroxy, there is a risk of a side-reaction between the hydroxy group and the acylating agent of formula (III). However, the reaction may be carried out under controlled conditions such that only the amine, $R_6^1NH—$ is acylated, for example, by using a $C_{2-9}$ acyloxy group as the leaving group $L_1$, in the acylating agent of formula (III) in the manner as previously described for an acid anhydride, and/or effecting the reaction at relatively low temperature, e.g. at below 10° C. Alternatively $R_3^1$ may be $C_{1-7}$ acyloxy in a compound of formula (II), although less preferably if $R_3$ in the resultant compound of formula (I) is to be hydroxy, and, after reaction with the acylating agent of formula (III), be converted into hydroxy, as described hereinafter.

When $R_9$ is $G(CH_2)_z$ where the variables are as hereinbefore defined, the leaving group G is a group that is displaceable by a secondary amino nucleophile adjacent to a carbonyl function. A preferred example is chloro.

The cyclisation reaction when $R_9$ is $G(CH_2)_z$ where the variables are as hereinbefore defined is preferably carried out in an inert solvent such as dimethylformamide.

In process variant (b), when $R_{10}$ in a compound of formula (IV) is $C_{1-6}$ alkyl, $C_{1-6}$ alkanoyl optionally substituted as hereinbefore defined, or phenyl optionally substituted as hereinbefore defined, the reaction between the compounds of formulae (II) and (IV) is, preferably, carried out in a solvent, such as methylene chloride, at below room temperature, in particular below 10° C.

When $R_{10}$ is hydrogen, the reaction between the compounds of formulae (II) and (IV) is, preferably, carried out using a corresponding alkali metal cyanate or thiocyanate, for example that of sodium or potassium, in an optionally methanolic aqueous medium acidified with a mineral acid, such as dilute hydrochloric acid. A slightly elevated temperature such as 50° to 90° C. is apt.

When Y in the resulting compound of formula (I) is cyano, Y' in the intermediate of formula (II) is preferably halo, such as bromo. The Y' halo substituent may subsequently be converted to cyano by nucleophilic displacement with cyanide ion, e.g. CuCN in an inert solvent such as dimethylformamide at elevated temperature. Such conversion is preferably effected before certain optional additional steps such as dehydration and cyclisation.

It will be appreciated that the labile nature of a Y or Q halo substituent will require the careful selection of process conditions for certain of the additional steps when Y is halo.

Y' or Q' may be amino, convertible to halo by the conventional Sandmeyer procedure, i.e. conversion of the amino group to a diazonium salt which is then reacted with acidic copper (I) halide in an aqueous medium.

When Y' is cyano, this may be converted by conventional methods to CHO, alkanoyl or alkoxycarbonyl. A CHO group may be formed by reduction by the 'Stephen Reaction' using Tin (II) chloride —HCl is ether at ambient temperature. An alkanoyl group may be formed by reaction with an appropriate organometallic reagent, such as a Grignard reagent. An alkoxycarbonyl group may be prepared by hydrolysis then esterification.

The reaction of the compounds of formulae (II) with (III) or (IV) results in a compound of formula (I) wherein $R_3$ is hydroxy, $C_{1-6}$ alkoxy or $C_{1-7}$ acyloxy. Examples of an optional conversion of $R_3$ in a compound of formula (I) into another $R_3$ are generally known in the art. For example, in compounds of formula (I) where Y is cyano, when $R_3$ is hydroxy, it may be alkylated using an alkyl iodide in an inert solvent, such as toluene, in the presence of a base, such as potassium hydroxide, or it may be acylated using a carboxylic acid chloride or anhydride in a non-hydroxylic solvent in the presence of antacid acceptor. Alternatively, when $R_3$ is $C_{1-7}$ acyloxy or $C_{1-6}$ alkoxy, it may be converted into hydroxy by conventional hydrolysis with, for example, dilute mineral acid.

The optional dehydration of the resulting compound of formula (I), wherein $R_3$ and $R_4$ are hydroxy and hydrogen respectively, into another compound of formula (I), wherein $R_3$ and $R_4$ together are a bond, may be carried out under conventional dehydration conditions, for example, by using a dehydrating agent, such as sodium hydride, in an inert solvent, such as dry tetrahydrofuran, at reflux temperature.

The optional reduction of the resulting compound of formula (I), wherein $R_3$ and $R_4$ together are a bond, into another compound of formula (I), wherein $R_3$ and $R_4$ are each hydrogen, may be carried out by hydrogenation using a catalyst of palladium on charcoal.

The optional thiation of the $R_6$—N—CO—$R_5$ group in a compound of formula (I) to give another compound of formula I, wherein X is sulphur, is, preferably, carried out with conventional thiation agents, such as hydrogen sulphide, phosporous pentasulphide and Lawesson's reagent (p-methoxyphenylthiophosphine sulphide dimer). The use of hydrogen sulphide and phosporous pentasulphide may lead to side-reactions and, therefore, the use of Lawesson's reagent is preferred.

The thiation reaction conditions are conventional for the thiation agent employed. For example, the use of hydrogen sulphide is, preferably, acid catalysed by, for example, hydrogen chloride in a polar solvent, such as acetic acid or ethanol. The preferred use of Lawesson's reagent is, preferably, carried out under reflux in a dry solvent, such as toluene or methylene chloride. The optional formation of a pharmaceutically acceptable salt, when the resulting compound of formula (I) contains a salifiable group, may be carried out conventionally.

A compound of formula (II) may be prepared by reacting a compound of formula (V):

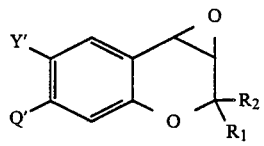

wherein Y', Q', $R_1$ and $R_2$ are as hereinbefore defined, with a compound of formula (VI):

 (VI)

wherein $R_6{}^1$ is as hereinbefore defined; optionally converting $R_3{}^1$ hydroxyl in the resulting compound of formula (II) into another $R_3{}^1$; and optionally converting Y' and/or Q' to other Y' and/or Q'.

The reaction is normally carried out in a solvent, such as a $C_{1-4}$ alcohol, in particular methanol, ethanol or propanol at an ambient or an elevated temperature, for example 12 to 100° C. The reaction proceeds particularly smoothly if carried out in ethanol under reflux.

The resulting compound of formula (II) may be removed from the reaction mixture by removal of the solvent, for example, by evaporation under reduced pressure. Any epoxide impurity may be removed conventionally, for example by chromatography.

The optional conversion of the hydroxy group for $R_3{}^1$ in the resulting compound of formula (II) into a $C_{1-6}$ alkoxy or $C_{1-7}$ acyloxy group may be carried out as described hereinbefore in relation to the corresponding conversion of $R_3$ in a compound of formula (I).

The optional conversions of Y' and/or Q' may be carried out as hereinbefore described.

A compound of formula (V) may be prepared by reacting a compound of formula (VII):

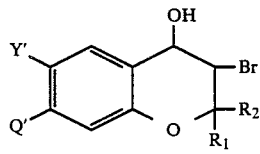

wherein Y', Q', $R_1$ and $R_2$ are as hereinbefore defined, the bromine atom being trans to the hydroxy group, with a base, such as potassium hydroxide, in a solvent, such as ether or aqueous dioxan.

A compound of formula (VII) may be prepared by reacting a compound of formula (VIII):

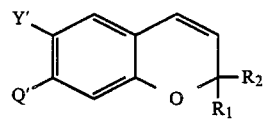

wherein Y', Q', $R_1$ and $R_2$ are as hereinbefore defined, with N-bromosuccinimide in a solvent, such as aqueous dimethyl sulphoxide.

A compound of formula (VIII) wherein Y' is halo and Q' is nitro may be prepared from a compound of formula (IX):

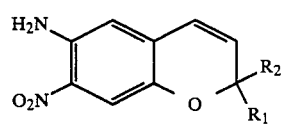

where $R_1$ and $R_2$ are as hereinbefore defined, by reaction with sodium nitrite in concentrated sulphuric acid and glacial acetic acid at a temperature below 10° C., followed by the appropriate cuprous halide in the corresponding hydrohalic acid.

The preparation of the compound of formula (IX) in which $R_1$ and $R_2$ are each methyl is described in J.Med.-Chem., 26,1582(1983), and the corresponding compounds having other $R_1$ and $R_2$ and compounds of formula (VIII) wherein Y' is other than halo and Q' is other than nitro are prepared analogously and as in J.Med. Chem., 27,1128 (1984).

As mentioned previously, some of the compounds of formula (I) may exist in optically active forms, and the processes of the present invention produce mixtures of such forms. The individual enantiomers may be resolved by conventional methods.

It is preferred that the compounds of formula (I) are isolated in substantially pure form.

Some of the intermediates of formulae (II), (V), (VII) or (VIII) (other than those described in the above references), wherein Y' is Y and Q' is Q are believed to be novel and represent part of the present invention. The intermediates of formulae (III), (IV) or (VI) are known and may be prepared in accordance with an appropriate known process.

As mentioned previously, the compounds of formula (I) have been found to have blood-pressure lowering activity. They are therefore useful in the treatment of hypertension.

The present invention accordingly provides a pharmaceutical composition which comprises a compound of formula (I) or a pharmaceutically acceptable salt thereof, and a pharmaceutically acceptable carrier. In particular, the present invention provides an anti-hypertensive pharmaceutical composition which comprises an anti-hypertensive effective amount of a compound of formula (I) or a pharmaceutically acceptable salt thereof, and a pharmaceutically acceptable carrier.

The compositions are preferably adapted for oral administration. However, they may be adapted for other modes of administration, for example parenteral administration for patients suffering from heart failure.

The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling or tabletting. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminum stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The present invention further provides a method of prophylaxis or treatment of hypertension in mammals including man, which comprises administering to the suffering mammal an anti-hypertensive effective amount of a compound of formula (I) or a pharmaceutically acceptable salt thereof.

An effective amount will depend on the relative efficacy of the compounds of the present invention, the severity of the hypertension being treated and the weight of the sufferer. However, a unit dose form of a composition of the invention may contain from 1 to 100 mg of a compound of the invention and more usually from 2 to 50 mg, for example 5 to 25 mg such as 6, 10, 15 or 20 mg. Such compositions may be administered from 1 to 6 times a day, more usually from 2 to 4 times a day, in a manner such that the daily dose is from 5 to 200 mg for a 70 kg human adult and more particularly from 10 to 100 mg.

No toxicological effects are indicated at the aforementioned dosage ranges.

The present invention further provides a compound of formula (I) or a pharmaceutically acceptable salt thereof for use in the treatment or prophylaxis of hypertension.

The following descriptions relate to the preparation of intermediates and the following examples relate to the preparation of a compound of formula (I).

DESCRIPTION 1

6-Bromo-2,2-dimethyl-7-nitro-2H-1-benzopyran (D1)

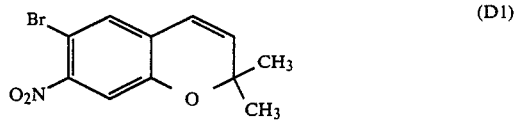

(D1)

A suspension of 6-amino-2,2-dimethyl-7-nitro-2H-1-benzopyran (5.0 g, the preparation of which was described in *J. Med. Chem.*, 26, 1582 (1983)) in glacial acetic acid (19 mL) was added dropwise to a stirred solution of sodium nitrite (1.6 g) in conc. $H_2SO_4$ (19 mL) while maintaining the temperature below 10° C. After an additional 0.5 h, the dark brown solution was added to a stirred solution of CuBr (6.5 g) in 47% HBr (53 mL). After 1 h, water was added to the solution and it was extracted with ethyl acetate. The organic extract was washed with water, saturated sodium bicarbonate solution, and dried over anh. $MgSO_4$. The organic layer was filtered, evaporated, and chromatographed on silica gel. Elution with 3% ethyl acetate—60°–80° C. petroleum ether gave the compound of description 1 as a crude solid (3.5 g). Mass spectrum (E.I.) M+ at m/z 282.9848. Calcd. for $C_{11}H_{10}NO_3Br$: 282.9845.

DESCRIPTION 2 trans-3,6-Dibromo-3,4-dihydro-2,2-dimethyl-7-nitro-2H-1-benzopyran-4-ol (D2)

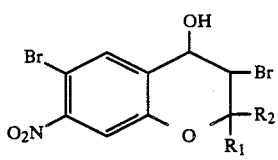
(D2)

The compound of description 1 (3.43 g) was dissolved in dimethyl sulphoxide (20 mL) and water (2 mL), and N-bromosuccinimide (6.0 g) added to the stirred solution. The resulting solution was stirred at room temperature for 18 h, diluted with water and extracted with EtOAc to give a crude mixture which was boiled in dioxan (60 mL) and water (30 mL) for 18 h. Dilution with water and extraction with ethyl acetate gave the compound of description 2 as a yellow solid (3.7 g). Recrystallisation of a small portion from EtOAc—60°–80° C. petroleum ether gave the analytical sample of
m.p. 113°–114° C.

Anal. $C_{11}H_{11}NO_4Br_2$ req.: C,34.67; H,2.91; N,3.68. Found: C,34.41; H,2.51; N,3.94%.

DESCRIPTION 3

6-Bromo-3,4-epoxy-3,4-dihydro-2,2-dimethyl-7-nitro-2H-1-benzopyran (D3)

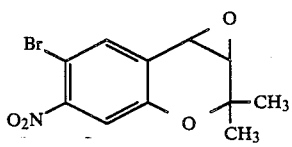
(D3)

The bromohydrin of description 2 (3.7 g) was dissolved in dry ether (500 mL) and potassium hydroxide pellets (4.0 g) added. The reaction mixture was stirred vigorously at room temperature for 48 h and then filtered and evaporated to give the epoxide of description 3 as a solid (2.47 g).

NMR (CDCl$_3$) δ 1.05 (2, 3H),
1.35 (s, 3H),
3.25 (d, J=4 Hz, 1H),
3.60 (d, J=4 Hz, 1H),
7.00 (s, 1H),
7.40 (s, 1H).

DESCRIPTION 4 trans-4-Amino-6-bromo-3,4-dihydro-2,2-dimethyl-7-nitro-2H-1-benzopyran-3-ol (D4)

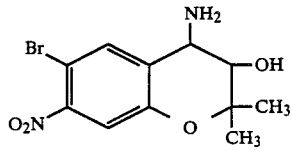
(D4)

The epoxide of description 3 (2.47 g) was dissolved in ethanol (50 mL) and 0.880 ammonia solution (40 mL) and the mixture stirred at room temperature for 4 days. The solvents were evaporated and the residue washed with ether to give the aminoalcohol of description 4 as a yellow solid (2.1 g).

Mass spectrum (EI) shows M$^+$ at m/z 316.0084. Calcd. for $C_{11}H_{13}N_2O_4Br$: 316.0059.

EXAMPLE 1 trans-4-Acetylamino-6-bromo-3,4-dihydro-2,2-dimethyl-7-nitro-2H-1-benzopyran-3-ol (E1)

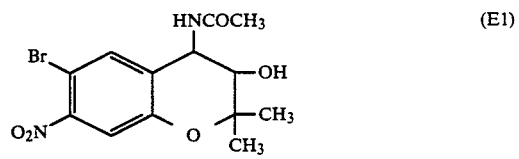
(E1)

The aminoalcohol of description 4 (2.0 g) and triethylamine (2.0 mL) were dissolved in dichloromethane (100 mL) and to this stirred solution was added acetyl chloride (0.5 mL). The solution was stirred for 18 h and water added. The layers were separated and the aqueous layer extracted with chloroform. The combined organic layers were washed with 2N HCl, sodium bicarbonate solution, water and brine and dried over anhydrous MgSO$_4$. Filtration and evaporation gave the acetylamino compound of example 1 as a yellow solid (2.1 g).

A portion of this solid was chromatographed (chromatotron, ethyl acetate-5% ethanol) to give a pure sample of m.p. 208°–210° C.

NMR (DMSOd$_6$) δ 1.06 (s, 3H),
1.28 (s, 3H),
1.82 (s, 3H),
3.40 (q, J=10,5, 1H),
4.58 (q, J=10,9, 1H),
5.48 (d, J=5, 1H),
7.23 (s, 2H),
8.08 (d, J=9, 1H).
Mass spectrum (E1) M$^+$ at m/z 358.0147. $C_{13}H_{15}N_2O_5Br$ req. 358.0164.

EXAMPLE 2 trans-4-Acetylamino-6-cyano-3,4-dihydro-2,2-dimethyl-7-nitro-2H-1-benzopyran-3-ol (E2)

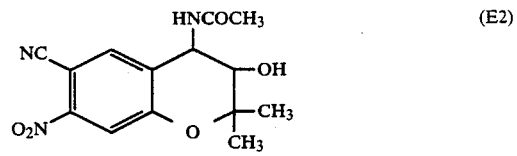
(E2)

The bromo compound of example 1 (0.36 g) was dissolved in dimethyl formamide (5 mL) and CuCN (0.1 g) added. The mixture was stirred at 100° C. for 6 h. The mixture was poured into water, and extracted with chloroform. The chloroform extract was washed with water, and brine, and dried over anhydrous MgSO$_4$. Filtration and evaporation gave a crude solid (70 mg). Trituration with ethyl acetate gave the compound of example 2 as a yellow solid (19 mg) of m.p. 209°–211° C.

NMR (DMSOd$_6$) δ 1.23 (s, 3H),
1.45 (s, 3H),
2.00 (s, 3H),
3.62 (q, J=9,5, collapsing to d,J=9 on addition of D$_2$O, 1H), 4.80 (t, J=9,9 collapsing to d, J=9 on addition of D$_2$O, 1H), 5.79 (d, J=5, 1H, exchangeable with D$_2$O)

7.73 (s, 1H), 7.75 (narrow m, 1H), 8.35 (d, J=9, 1H, exchangeable with D$_2$O).

PHARMACOLOGICAL DATA

Systolic blood pressures were recorded by a modification of the tail cuff method described by I. M. Claxton, M. G. Palfreyman, R. H. Poyser, R. L. Whiting, European Journal of Pharmacology, 37, 179 (1976). A W+W BP recorder, model 8005 was used to display pulses. Prior to all measurements rats were placed in a heated environment (33.5°±0.5° C.) before transfer to a restraining cage. Each determination of blood pressure was the mean of at least 6 readings. Spontaneously hypertensive rats (ages 12–18 weeks) with systolic blood pressures >170 mmHg were considered hypertensive.

| Compound of Example 2 | Time Post Dose Hrs | % Change in Systolic Blood Pressure |
|---|---|---|
| 6 Rats | 1 | −46 ± 5 |
| Dose 0.3 mg/kg po | 2 | −43 ± 4 |
| Initial Blood | 4 | −38 ± 4 |
| Pressure | 6 | −26 ± 5 |
| 269 ± 6 mmHg | | |

What is claimed is:

1. A compound of formula (I) or, when the compound of formula (I) contains a salifiable group, a pharmaceutically acceptable salt thereof:

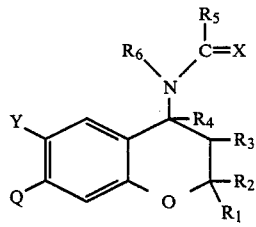

(I)

wherein:

one of R$_1$ and R$_2$ is hydrogen or C$_{1-4}$ alkyl and the other is C$_{1-4}$ alkyl or R$_1$ and R$_2$ together are C$_{2-5}$-polymethylene;

either R$_3$ is hydrogen, hydroxy, C$_{1-6}$ alkoxy or C$_{1-7}$ alkanoyloxy and R$_4$ is hydrogen or R$_3$ and R$_4$ together are a bond;

R$_5$ is hydrogen; C$_{1-6}$ alkyl optionally substituted by halogen, hydroxy, C$_{1-6}$ alkoxycarbonyl, carboxy or amino optionally substituted by one or two independent C$_{1-6}$ alkyl groups, or C$_{2-6}$ alkenyl; amino optionally substituted by a C$_{1-6}$ alkyl or C$_{2-6}$ alkenyl group or by a C$_{1-6}$ alkanoyl group optionally substituted by up to three halo atoms, or by a phenyl group optionally substituted by C$_{1-6}$ alkyl, C$_{1-6}$ alkoxy or halogen; or a member selected from the group consisting of phenyl, naphthyl, furyl, thienyl, pyrryl, oxazolyl, thiazolyl, imidazolyl, thiadiazolyl, pyridyl, pyridazyl, pyrimidyl, pyrazyl, triazyl, benzofuranyl, benzothienyl, indolyl, indazolyl, quinolyl, isoquinolyl and quinazonyl, said member being optionally substituted by one or more groups or atoms selected from the class of C$_{1-6}$ alkyl, C$_{1-6}$ alkoxy, hydroxy, halogen, trifluoromethyl, nitro, cyano, C$_{1-12}$ carboxylic acyl, or amino or aminocarbonyl optionally substituted by one or two C$_{1-6}$ alkyl groups;

R$_6$ is hydrogen or C$_{1-6}$ alkyl;

X is oxygen or sulphur;

Y and Q are halo, cyano, CHO, C$_{2-7}$ alkanoyl or C$_{1-6}$ alkoxycarbonyl; and the nitrogen-containing group in the 4-position being trans to the R$_3$ group when R$_3$ is hydroxy, C$_{1-6}$ alkoxy or C$_{1-7}$ alkenoyloxy.

2. A compound according to claim 1 wherein R$_1$ and R$_2$ are both methyl.

3. A compound according to claim 1 wherein R$_3$ and R$_4$ together are a bond, or R$_3$ is hydroxy and R$_4$ is hydrogen.

4. A compound according to claim 1 wherein R$_5$ is methyl or R$_5$ is phenyl or amino, either being optionally substituted as defined in claim 1; and R$_6$ is methyl, ethyl or hydrogen.

5. A compound selected from trans-4-acetylamino-6-bromo-3,4-dihydro-2,2-dimethyl-7-nitro-2H-1-benzopyran-3-ol and trans-4-acetylamino-6-cyano-3,4-dihydro-2,2-dimethyl-7-nitro-2H-1-benzopyran-3-ol.

6. An anti-hypertensive pharmaceutical composition comprising an effective amount of a compound according to claim 1 or a pharmaceutically acceptable salt thereof, and a pharmaceutically acceptable carrier.

7. A method of treatment of hypertension in mammals, which comprises the administration of an anti-hypertensive effective amount of a compound of formula (I) as defined in claim 1, or a pharmaceutically acceptable salt thereof.

* * * * *